Figure 1:
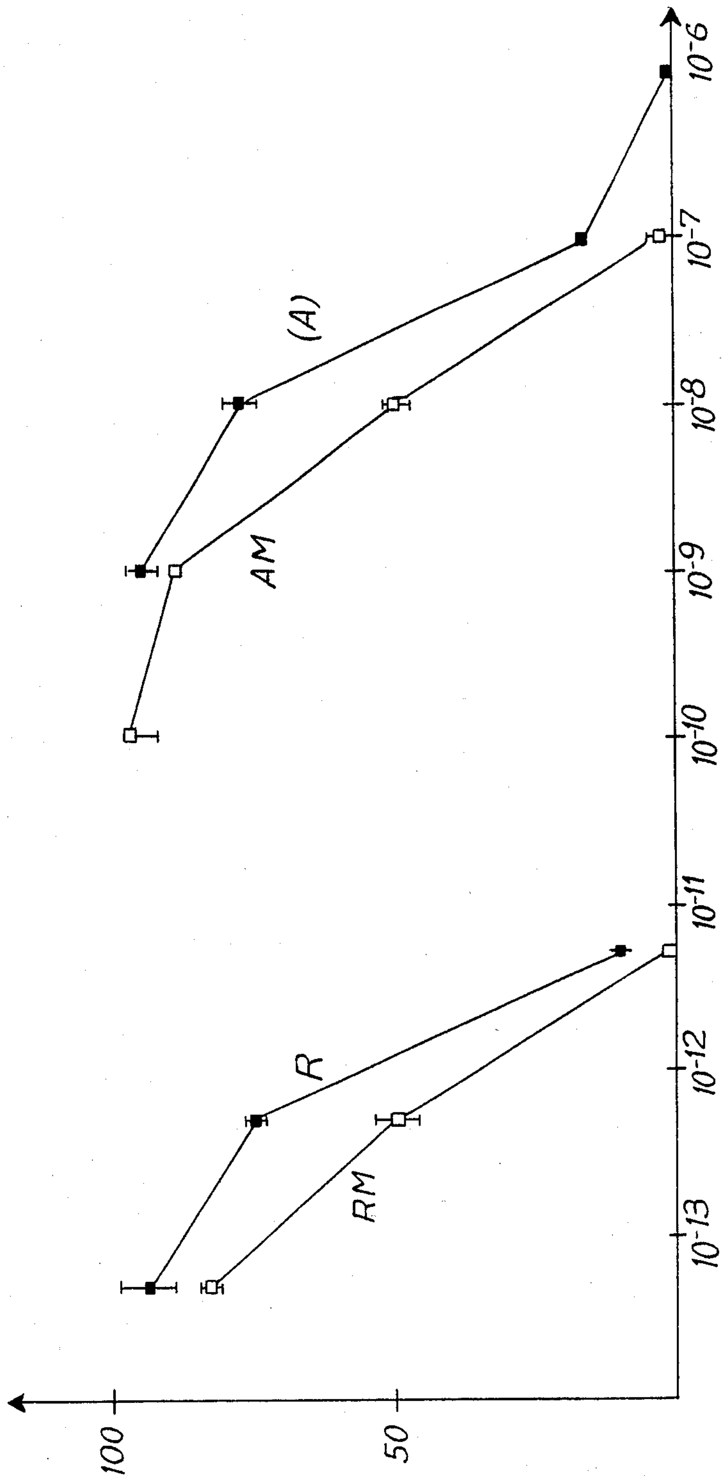

United States Patent [19]

Jansen et al.

[11] Patent Number: 4,614,650

[45] Date of Patent: Sep. 30, 1986

[54] CYTOTOXIC COMPOSITION INCLUDING AT LEAST AN IMMUNOTOXINE AND AN AMINE

[75] Inventors: Franz Jansen, Assas; Pierre Gros, Montpellier, both of France

[73] Assignee: Sanofi, Paris, France

[21] Appl. No.: 557,148

[22] PCT Filed: Mar. 7, 1983

[86] PCT No.: PCT/FR83/00043

§ 371 Date: Nov. 9, 1983

§ 102(e) Date: Nov. 9, 1983

[87] PCT Pub. No.: WO83/03200

PCT Pub. Date: Sep. 29, 1983

[30] Foreign Application Priority Data

Mar. 11, 1982 [FR] France ........................ 82 04119

[51] Int. Cl.4 ........................ A61K 39/00

[52] U.S. Cl. ........................ 424/85; 530/390

[58] Field of Search ........... 424/85; 260/112 B, 112 R

[56] References Cited

U.S. PATENT DOCUMENTS 4,485,093 11/1984 Runje ........................ 260/112 R 4,489,710 12/1984 Spitter ........................ 128/1 R 4,490,362 10/1984 Shionoya et al. ........................ 424/85

FOREIGN PATENT DOCUMENTS 0080401 6/1983 European Pat. Off. .

2466252 4/1981 France .

OTHER PUBLICATIONS

Biological Abstracts vol. 73, 1982 Schneider et al, Effect of . . . Fibroblast.

Biological Abstracts, vol. 73, 1982 (Philadelphia, PA) Y. J. Schneider et al.: "Effect of Chloroquine and Methylamine on Endocytosis of Fluorescein-Labelled Control Immunoglobulin G and of Anti-Plasma Membrane Immunoglobulin G by Cultured Fibroblasts", voir resume 78102, Eur. J. Biochem. 1981, 118(1), 33-38.

*Primary Examiner*—John Kight

*Assistant Examiner*—Garnette D. Draper

*Attorney, Agent, or Firm*—Stevens, Davis, Miller & Mosher

[57] ABSTRACT

The present invention relates to cytotoxic medicines characterized in that they contain in association at least an immunotoxine and an amine or a pharmaceutically acceptable salt of said amine.

4 Claims, 3 Drawing Figures

CYTOTOXIC COMPOSITION INCLUDING AT LEAST AN IMMUNOTOXINE AND AN AMINE

The present invention relates to cytotoxic drugs comprising at least one immunotoxin and one amine of formula $R_1NHR_2$ in which $R_1$ represents hydrogen or a lower alkyl group (having 1 to 4 carbon atoms), $R_2$ represents a lower alkyl group or the group $R_1NHR_2$ represents 1-amino adamantane.

Earlier French Patent Applications, particularly Nos. 78 27838, 79 24655, 81 07596 and 81 21836, describe the preparation of so-called conjugate anti-cancerous products obtained by coupling, by covalent bond, of the chain A of ricin with antibodies or fragments of antibodies directed against an antigen carried by a cell to be destroyed. The products of this type are designated in the present Application under the generic name of immunotoxins.

Chain A of ricin/antibody conjugates are prepared by associating by means of a covalent bond of the disulphide type, on the one hand, an immunoglobulin which is specific for a given antigen, or any fragment of this molecule which possesses the capacity of specific recognition with respect to the antigen, with, on the other hand, the A chain of ricin. The choice of a disulphide bond between the A chain and the immunoglobulin is based on the following arguments:

- this type of bond is the type which exists in the natural ricin molecule, and it can be expected to be particularly suitable for presenting the A chain in a conformation which facilitates its penetration into the cell, whilst at best retaining its fundamental biological property of inhibiting protein synthesis,
- this type of bond is biochemically labile, which provides the A chain, coupled in this way, with the possibility of being liberated, from its carrier protein, in the contents of the cell,
- the A chain of ricin possesses a single cysteine residue in its structure and hence only the SH group capable of creating a disulphide bond. Consequently, the conjugates formed by involving this SH group in a disulphide bridge will be chemically well defined and will in no way modify the structure of the A chain, thus ensuring the integral retention of its biological activity, and
- there are efficient methods which make it possible to produce such a disulphide bond under conditions which are sufficiently mild to ensure the integrity of the biological properties of the protein constituents of the conjugates formed.

In order to produce such conjugates, the proteins to be coupled must each carry at least one sulphur atom which is naturally capable, or is artificially rendered capable, of creating the desired disulphide bond, whether these sulphur atoms already exist in the proteins or have been chemically introduced into these proteins. As indicated above, the A chain of ricin naturally possesses only one sulphur atom permitting the desired coupling. This is the sulphur atom in the thiol group of the single cysteine residue incorporated in the A chain. As regards the immunoglobulin or its fragments, several cases must be considered:

(1) In the case of an entire immunoglobulin, neither a free thiol group nor other sulphur atoms capable of being used for the coupling exist naturally in these proteins. It will therefore be necessary, in this case, to introduce one or more sulphur atoms into the immunoglobulin molecule artificially so that:

- the biological properties of the immunoglobulin are not profoundly impaired, and
- this sulphur atom, or these sulphur atoms, can subsequently be involved in the disulphide bond to be established with one or more molecules of the A chain of ricin.

(2) In the case of a Fab fragment, the situation is absolutely identical to that described above.

(3) If a fragment of the Fab' type is employed, it is possible to use the sulphur atom present in the free thiol group to carry out the coupling to the A chain. However, it is also possible to use the artificial introduction of one or more sulphur atoms; in this case, it is necessary to block the free thiol group in a stable manner beforehand, for example by alkylation.

(4) Finally, if it is desired to couple a $F(ab')_2$ fragment of immunoglobulin, it is necessary, as in the case of the whole immunoglobulin, to introduce one or more sulphur-containing groups into $F(ab')_2$ artificially.

In all the cases in which one or more sulphur-containing radicals are introduced into the immunoglobulin or its fragments, it is necessary to avoid any substitution in the site for recognition of the antigen or in its immediate environment, which substitution could disturb the recognition properties of the antibody. In order to exclude this risk, the site for recognition of the antigen can be blocked temporarily, during the substitution reaction, by treating the antibody beforehand with the specific antigen, or with another antigen which possesses an adequate cross-reaction, or with a suitable hapten.

The operation for temporary protection can be carried out:

- either in the liquid phase, if the antibody-antigen (or hapten) complex is soluble in the reaction medium,
- or in the heterogeneous phase, if this complex is spontaneously insoluble or also if it has been deliberately rendered insoluble by means of a suitable procedure, in particular by fixing the antigen (or hapten) to an insoluble support so that the modified support thus obtained possesses an adequate affinity for the antibody.
- After the substitution step, it will be necessary to unblock the site for recognition of the antigen, on the antibody, by means of a suitable procedure for removing the antigen, in order to regenerate the capacity of the antibody for specific recognition.

To produce the disulphide bridge between the two proteins, it is not possible to bring the two constituents of the conjugate, each carrying a SH group, into contact with one another and to carry out an oxidation. In fact, under these conditions, the coupling reaction is an equilibrium reaction which is very difficult to drive to completion. Furthermore, the desired reaction is accompanied by the formation of polymers of each of the two constituents, which would result in a very low yield of the desired product and the presence of impurities which are very difficult to remove.

According to the invention, the conjugate is prepared by bringing one of the proteins, carrying its free SH group, into contact with the other protein, in which the SH group is activated by conversion into a mixed disulphide with a suitable sulphur-containing organic radical. The preparation of the conjugate can be represented by the equation:

$$P_1\text{-}SH + P_2\text{-}S\text{-}S\text{-}X \rightarrow P_1\text{-}S\text{-}S\text{-}P_2 + XSH$$

in which $P_1$ and $P_2$ represent the two proteins to be coupled and X denotes the activator radical. It is immediately apparent from this equation that, in each case, the coupling reaction can be carried out in accordance with two variants, depending on whether $P_1$ represents the immunoglobulin or its fragment and $P_2$ represents the A chain of ricin, or vice versa.

Case in which $P_1$ represents the antibody or a fragment and $P_2$ represents the A chain of ricin To activate the free SH in the A chain of ricin, the solution of A chain, prepared as indicated above, is used, and it is subjected to an exchange reaction:

$$ASH+XSSX \rightleftharpoons A\text{-}S\text{-}S\text{-}X+XSH \quad (1)$$

in which ASH represents the A chain of ricin and X represents the activator radical.

In particular, X can denote a pyrid-2- or -4-yl group which is optionally substituted by one or more alkyl or halogen radicals or carboxylic acid groups, or X can also represent a phenyl nucleus which is optionally substituted by one or more nitro or carboxylic acid groups. Reaction (1) is an equilibrium reaction but the equilibrium can easily be displaced towards the right by using a large molar excess of the reagent XSSX, which is generally inexpensive and readily accessible. It is possible to monitor the course of reaction (1) by ultraviolet or visible spectrophotometry because the compound XSH which is formed shows an intense absorption in this region. When the reaction has reached the desired degree of completion, the excess of the reagent X-S-S-X, and also the reaction product X-SH, are removed by dialysis or filtration on a molecular sieve in gel form. Finally, a pure solution of the compound A-S-S-X in the chosen buffer is obtained. If necessary, this solution can be kept for several weeks after freezing.

The immunoglobulin substituted by a SH group is also prepared. To do this, the solution of immunoglobulin obtained above is used either as such or after blocking its site for the recognition of the antigen, with the corresponding hapten, followed by removal of the excess hapten. By reacting S-acetylmercaptosuccinic anhydride with this protein, it is possible to fix one or more S-acetylmercaptosuccinyl groups, per molecule of protein, by means of its free amino groups, and then to liberate the thiol groups by the action of hydroxylamine, as has been described [Archives of Biochemistry and Biophysics 119, 41–49 (1967)]. Dialysis makes it possible to remove the excess reagents and also the reaction products of low molecular weight.

All these operations are carried out in a phosphate buffer at pH=7.0 and at temperatures which do not exceed ambient temperature. The hapten which may have been used as a temporary blocking agent is removed from the solution finally obtained. If it proves necessary, this solution can be concentrated, for example by ultrafiltration. The coupling between the two reagents thus prepared is effected by simple contact in aqueous solution, at ambient temperature, for a time varying from a few hours to one day, in accordance with the equation:

(4)

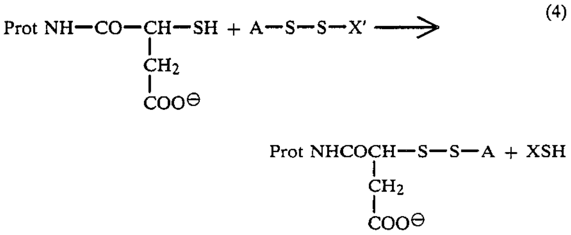

The course of the reaction is followed by spectrophotometric determination of the compound XSH formed. The latter is removed by dialysis and a solution of the expected conjugate is obtained which must be further purified. In fact, it is essential, in particular, to remove the molecules of A-S-S-X which have not reacted and which, if they were present in the conjugate, could give rise to a non-selective toxicity.

The purification can be effected by various known methods such as fractional precipitation with the aid of water-miscible organic solvents or of salts, gel permeation chromatography, or also affinity chromatography on a column formed by an insoluble support on which the antigen (or the hapten) is fixed, against which antigen the antibody employed in the preparation of the conjugate is directed.

These purification methods can be applied directly to the dialysed solution originating from the coupling step. However, better results are obtained, and, in particular, the subsequent formation of polymers of the conjugate is avoided, by the prior blocking of the SH groups which remain free, with a reagent such as N-ethylmaleimide.

Case in which $P_1$ represents the A chain of ricin and $P_2$ represents the antibody In this case, the products required for the coupling area the A chain of ricin and the immunoglobulin (or its fragment), which is substituted by a group carrying one or more activated sulphur atoms. The A chain of ricin is used as obtained by the purification procedure described. The immunoglobulin substituted by an activated sulphur atom is prepared from the immunoglobulin itself by substitution with the aid of a reagent which itself carries an activated sulphur atom, in accordance with the equation:

$$Prot+Y\text{-}R\text{-}S\text{-}S\text{-}X \rightarrow Prot\text{-}R\text{-}SS\text{-}X$$

in which Prot denotes the immunoglobulin, Y represents a group permitting the covalent fixation of the reagent to the protein, R denotes a group which can simultaneously carry the substituents Y and -S-SX, and X denotes the activator radical.

A reaction of this type has already been used for coupling two proteins (identical or different) by means of a disulphide bridge, but the application of this principle to the coupling of an immunoglobulin with the A chain of ricin is new.

The functional group Y is a group which is capable of bonding in a covalent manner with any one of the groups carried by the side chains of the constituent aminoacids of the protein to be substituted. Amongst these latter groups, the terminal amino groups of lysyl radicals, which are present in the protein, are particularly indicated. In this case, Y can represent, in particular:

a carboxylic acid group which can bond to the amino groups of the protein in the presence of a coupling agent such as a carbodiimide and, in particular, a water-soluble derivative such as 1-ethyl-3-(3-diethylaminopropyl)-carbodiimide, a carboxylic acid chloride which is capable of reacting directly with the amino groups in order to acylate them, a so-called "activated" ester, such as an ortho- or para-, nitro- or dinitro-phenyl ester or also a N-hydroxy-succinimide ester, which reacts directly with the amino groups in order to acylate them, an internal anhydride of a dicarboxylic acid, such as, for example, succinic anhydride, which reacts spontaneously with the amino groups in order to create amide bonds, or an iminoester group

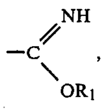

in which $R_1$ is an alkyl group which reacts with the amino groups of the protein in accordance with the equation

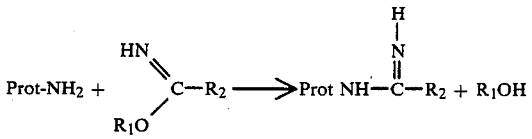

X denotes functional group which is capable of reacting with a free thiol radical.

In particular, X can denote a pyrid-2-yl or pyrid-4-yl group which is optionally substituted by one or more alkyl, halogen or carboxylic acid radicals. X can also denote a phenyl group which is preferably substituted by one or more nitro or carboxylic acid groups. X can also represent an alkoxycarbonyl group such as the methoxycarbonyl group.

The radical R denotes any radical which is capable of simultaneously carrying the substituents Y and S-S-X. The radical chosen must not contain groups which are capable of interfering, in the course of the subsequent reactions, with the reagents used and the products synthesized. In particular, the group R can be a group $-(CH_2)_n$, in which n is between 2 and 10, or also a group

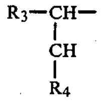

in which $R_4$ denotes hydrogen or an alkyl group having from 1 to 8 carbon atoms, and $R_3$ denotes a substituent which is inert towards the reagents subsequently used, such as an amide group

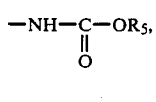

in which $R_5$ denotes a linear or branched alkyl group having from 1 to 5 carbon atoms, in particular the tert.-butyl group.

The reaction of the compound Y-R-S-S-X with the immunoglobulin is carried out in the homogeneous liquid phase, most frequently in water or a buffer solution. When required by the solubility of the reagents, it is possible to add, to the reaction medium, up to 20% by volume of a water-miscible organic solvent such as an alcohol, in particular tertiary butanol.

The reaction is carried out at ambient temperature for a time which varies from a few hours to 24 hours. Thereafter, dialysis makes it possible to remove the products of low molecular weight and, in particular, the excess reagents. This process makes it possible to introduce a number of substituent groups of between 1 to 5 per molecule of protein.

Using such compounds, the coupling with the A chain of ricin is carried out by bringing the two proteins into contact with one another in aqueous solution, at a temperature which does not exceed 30° C., for a time which varies from a few hours to one day. The reaction takes place in accordance with the equation:

$$\text{Prot-R-S-S-X} + \text{ASH} \rightarrow \text{Prot-R-S-S-A} + \text{XSH}$$

in which Prot-R-S-S-X represents the substituted immunoglobulin (or its fragment), activated on the sulphur atom, and ASH represents the A chain of ricin. The solution obtained is dialysed in order to remove the products of low molecular weight, and the conjugate can then be purified by various known methods, as indicated in the first process for the preparation of the conjugates.

French Application No. 81 21836 further described the property of the ammonium ions (in the form of any of their salts and in particular the chloride) of efficiently potentializing the cytotoxic action of these immunotoxins.

In French Patent Application No. 82 02091 of Feb. 9, 1982, Applicants described the property of the substances belonging to the class of carboxylic ionophores of potentializing the activity of the immunotoxins and of accelerating their kinetics of action.

The present invention has for its object the preparation of powerful cytotoxic drugs using the potentialization of the selective cytotoxic effects of the immunotoxins described in the earlier Patent Applications; in fact, it has been found that the amines defined above used in the form of one of their pharmaceutically acceptable salts and at doses where they themselves do not present any inherent cytotoxicity for the lines studied, were extremely powerful potentializers and accelerators of the cytotoxic effect of the immunotoxins.

The following non-limiting examples enable the scope of the invention to be more readily understood.

EXAMPLE 1

Conjugate obtained by reaction between a human anti-cell T antibody (antibody directed against the antigen T65) substituted by an activated disulfide group and the chain A of ricin.

(a) Human anti-cell T antibody (or antibody T101)

This antibody was obtained according to the method described in the Journal of Immunology 125 (2), 725–737 (1980).

It undergoes ultimate purification by dialysis against a PBS buffer (10 mM of phosphate, 140 mM of sodium chloride, pH 7.4).

(b) Chain A of ricin

The chain A of ricin was prepared and purified as indicated in Applicants' earlier Applications (Patent No. 78 27838 and Addition No. 79 24655).

(c) Activated human anti-cell T antibody

To 0.5 ml of a solution of 14.2 mg/ml of 3-(2-pyridyl disulfanyl) propionic acid in tertiary butanol is added 0.1 ml of a solution of 42.7 mg/ml of 1-ethyl 3-(3-dimethylamino propyl) carbodiimide and the solution is left for 3 minutes at ambient temperature.

180 ul of the solution thus obtained are added to 5.6 ml of a solution of antibody at 3.6 mg/ml in the PBS buffer. Incubation is allowed to continue for 20 hours at 30° C.

The solution is then continuously dialysed for 3 days against 21 liters of PBS buffer at 4° C. 16 mg of activated antibody are thus obtained at a concentration of 2.6 mg/ml.

By spectrophotometric assay at 343 mm of the pyridine 2-thione released by exchange with the reduced glutathion, it is observed that an antibody carrying 3.1 activator groups per mole of antibody is obtained.

(d) Conjugate

To 4.6 ml of a solution of activated antibody in the PBS buffer (concentration 2.6 mg/ml, or 12 mg of activated antibody) is added 0.87 ml of a solution of chain A of ricin in the same buffer (concentration 6.6 mg/ml) and incubation is carried out at 25° C. for 20 hours.

The reaction mixture is chromatographed over a Sephadex G100 gel column. In each fraction, the concentration in antibody is determined by spectrophotometry at 280 nm and that of the chain A is determined by its power of inhibition of the proteo-synthesis measured on an acellular system. The identical fractions containing the conjugate are brought together and about 11 mg of the conjugate at the concentration of 0.8 mg/ml are obtained.

The analytic determinations made show that the solution contains 140 ug/ml of biologically active chain A, or about 1.1 mole of chain A per mole of antibody.

A study made by cytofluorometry further showed that the human anti-cell T antibody used, the corresponding activated antibody and the conjugate of this antibody with the chain A of ricin present superposable histograms of fluorescence which affirm that the antibody has not undergone any considerable alteration in the course of the reactions of activation and of coupling to which it was subjected and in particular that it remains capable, within the conjugate itself, of recognizing the human antigen T against which it is directed.

EXAMPLE 2

This example demonstrates the potentialization of the selective cytotoxicity of the anti-T65 immunotoxin (prepared as described in the previous example) with respect to human lymphoblastoid T cells of the line CEM carrying the T65 antigen by methylamine.

In these experiments, the cytotoxicity was assessed by measuring the incorporation of $^{14}C$-leucine by the cells after 18 hrs. of incubation at 37° C. in the presence of known quantities of the immunotoxin studied, or of cytotoxic substances of reference, in the absence or the presence of methylamine.

I-Potentialization of the cytotoxic effect by methylamine

The results of these experiments are presented in the form of dose/effect curves presenting on the y-axis the cytotoxic effect assessed as indicated above by the incorporation of the tracer, calculated in % of the value obtained on the control cells without cytotoxic substance and on the x-axis the molar concentrations in toxic sub-unit of the cytotoxic substances studied. The methylamine was tested at the concentration of 10 millimolars. It was previously checked that the methylamine is not spontaneously cytotoxic for the cells employed at the concentration indicated.

FIG. 1 shows the respective results obtained for
the chain A of ricin (A)
the ricin (R)
the chain A of ricin and methylamine (AM)
the ricin and methylamine (RM).

FIG. 1 shows the effect of methylamine on the inherent cytotoxicity of ricin and the isolated chain A, taken as reference substances. The values of the molar concentrations (C150) corresponding to 50% of inhibition of incorporation of the tracer are indicated in Table I.

TABLE I

| Substances tested | With methylamine 10 mM | Without methylamine |
|---|---|---|
| Ricin | $5 \cdot 10^{-13}$ M | $1.2 \cdot 10^{-12}$ M |
| Chain A | $1 \cdot 10^{-8}$ M | $2.6 \cdot 10^{-8}$ M |

These results demonstrate a very weak potentializer effect of the methylamine on the cytotoxicity of ricin (factor of potentialization of 2.4) and of chain A (factor of potentialization of 2.6).

Figure 2:
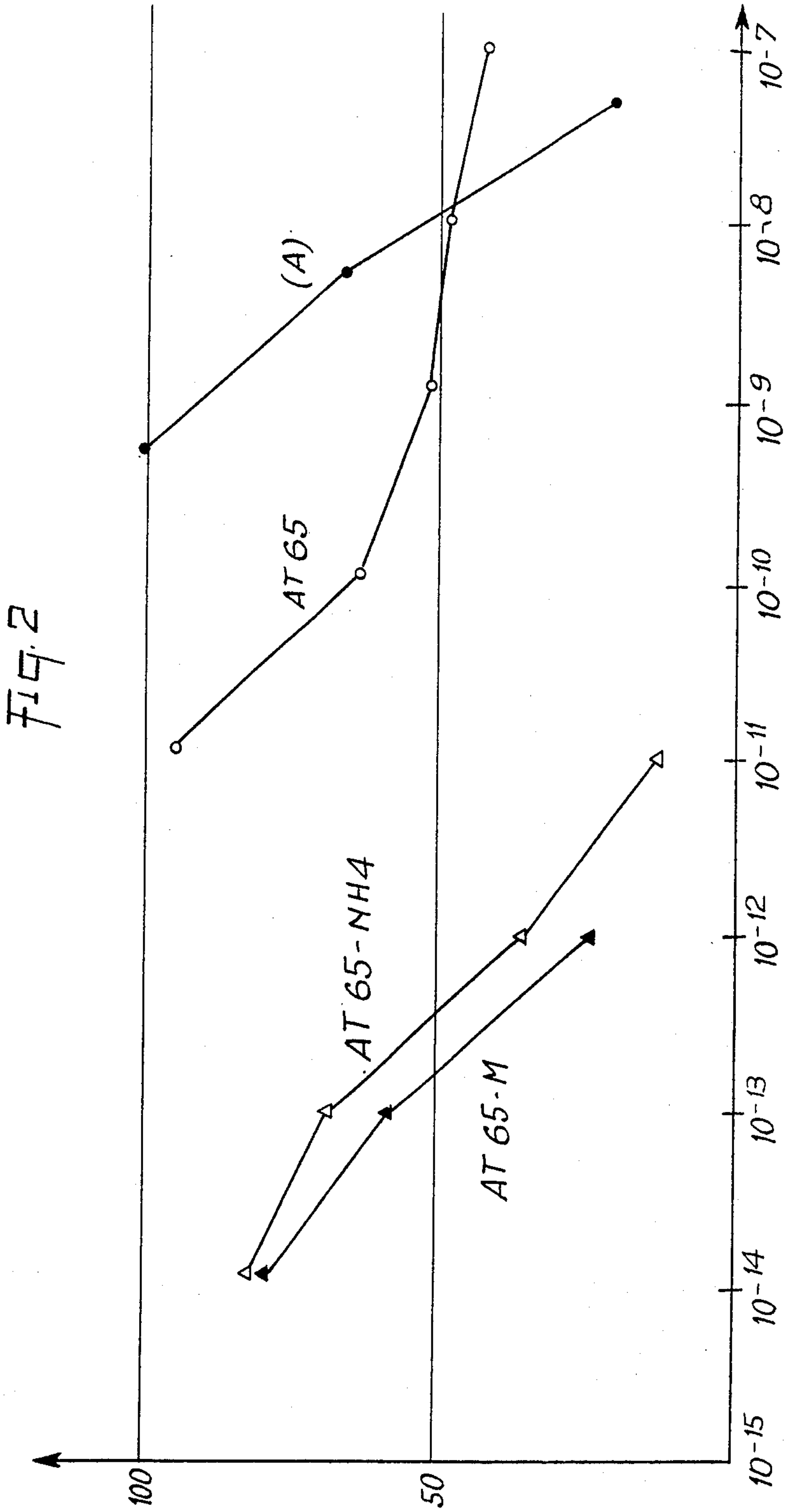

FIG. 2 shows the respective results obtained for:
the chain A of ricin (A)
the anti-T65 conjugate (AT65)
the anti-T65 conjugate mixed with the ammonium ion ($At65-NH_4$)
the anti-T65 conjugate mixed with methylamine (AT65-M).

FIG. 2 shows the compared potentializer effect of the $NH_4^+$ion (10 mM) and of methylamine (10 mM) on the cytotoxicity of the anti-T65 immunotoxin with respect to the cells of the line CEM. The values of the molar concentrations (C150) corresponding to 50% of inhibition of incorporation of the tracer are shown in Table II.

TABLE II

| Potentialization substances tested | C150 |
|---|---|
| None | $5 \cdot 10^{-9}$ M |
| $NH_4^+$ 10 mM | $3 \cdot 10^{-13}$ M |
| Methylamine 10 mM | $1.5 \cdot 10^{-13}$ M |

These results that the potentializer effect of methylamine is close to that of the ammonium ion and of the order of a factor of 13,000. This factor is considerably higher than those observed with ricin or the isolated chain A. This means that, in the presence of methylamine, the anti-T65 immunotoxin is, with respect to its specific target, a cytotoxic agent nearly 3 times more powerful than the ricin itself.

In addition, methylamine presents the remarkable property not only of potentializing the activity, but also of increasing the selectivity of the immunotoxin. If in fact the ratio of the C150s of the free chain A and of the immunotoxin is taken as criterion of selectivity of action of the immunotoxin, this ratio is of the order of 5 in the absence of methylamine and close to 65,000 in the presence of methylamine.

2 Acceleration of the kinetics of cytotoxicity of methylamine

The effect of the methylamine is not limited to considerably increasing the cytotoxic activity of the immunotoxins. This substance also makes it possible considerably to accelerate the kinetics of cytotoxicity of the immunotoxins, as shown by the following experiment.

Figure 3:
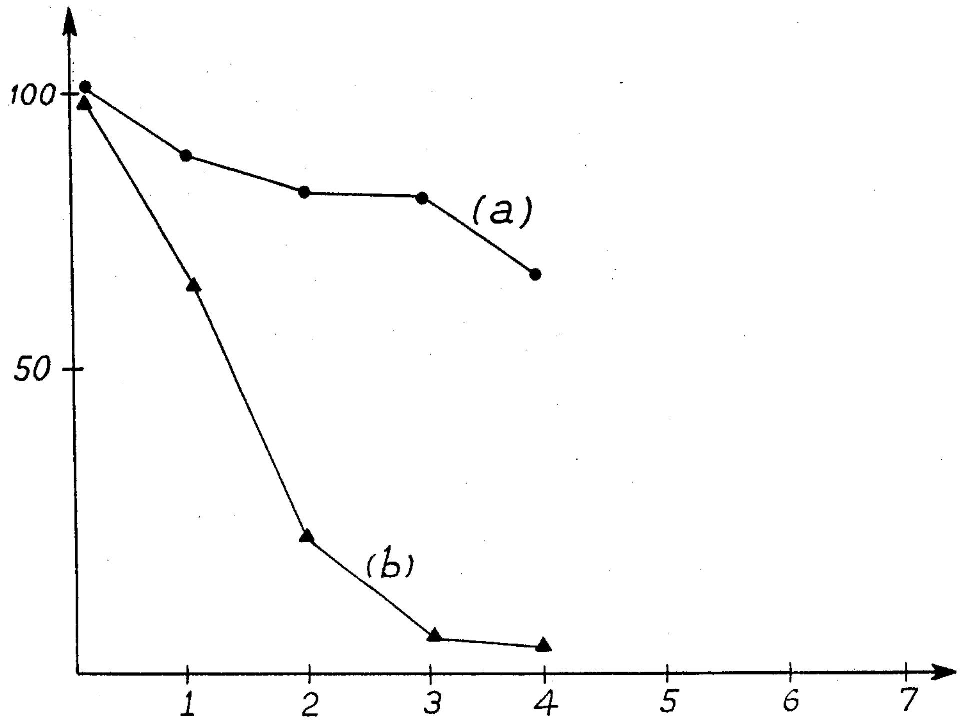

In this experiment, the incorporation of radioactive tracer in the cells was measured as previously, but this time as a function of the incubation time of the cells with the immunotoxin, in the absence and in the presence of methylamine 10 mM as potentializer. This experiment was carried out on the cellular model constituted by the human lymphoblastoid line CEM with the anti-T65 immunotoxin at the concentration of 50 mM. The results are shown in FIG. 3.

This Figure shows the results obtained, plotting on the y-axis the % of incorporation of $^{14}C$-leucine (% of the controls) and on the x-axis the time (in hours).

For this line, it appears that, in the absence of potentialization, the kinetics of cytotoxicity are very slow as shown by curve a. (Other experiments under the same conditions have shown that the time necessary for obtaining 50% of reduction of the incorporation of the tracer was of the order of 20 hrs.). On the contrary, in the presence of methylamine, a spectacular acceleration of the kinetics is manifested (curve b) since the time necessary for obtaining 50% of inhibition of incorporation is in that case of the order of 1.5 hrs. only.

Such an effect of acceleration is of the greatest importance for all applications of the immunotoxins and in particular for therapeutic applications in vivo, as the rapidity of action of the drug is always a factor very favourable to the efficiency of the treatment.

EXAMPLE 3

By operating as in Example 1 but by varying the amine used, the potentialization of the cytotoxic effect by an amine was determined (Example 1, point 1). The potentializer effect, expressed in C150 (cf. Table I) with the anti-T65 immunotoxin, is shown in Table III.

TABLE III

| Potentializer | Molar concentration amine | C150 (molar) |
|---|---|---|
| without | — | $5 \cdot 10^{-9}$ |
| dimethylamine | $10^{-2}$ | $3 \cdot 10^{-12}$ |
| 1-amino adamantane | $10^{-3}$ | $8 \cdot 10^{-12}$ |

The association constituted by an immunotoxin and an amine such as defined in the form of any one of its salts may therefore be used as a drug in human therapeutics. It may be used for the treatment of disorders, cancerous or not, which are sensitive to the antibody used for the preparation of the immunotoxin.

Aiming at eliminating all the cancerous cells, the treatment will be carried out with a sufficient dose of immunotoxin associated with a quantity of amine which may vary from 10 mg to 2 g (expressed as the base) for every administration of immunotoxin. The duration of the treatment must be determined in each case as a function of the subject and the nature of the disorder to be treated.

The novel drugs according to the invention are packaged for use by the injectable route and preferably by the intravenous route.

The constituents of the association will preferably be kept separate and mixed, only at the moment of use, in the syringe or the perfusion solvent.

What is claimed is:

1. A cytotoxic composition comprising a cytotoxic amount of an immunotoxin and 10 mg to 2 g of an amine of the formula $R_1NHR_2$ in which $R_1$designates hydrogen or lower alkyl and $R_2$ designates lower alkyl, or the formula $R_1NHR_2$ represents 1-aminoadmantane, said amine being used in the form of the amine or a pharmcentically acceptable amine scale, said immunotixin comprising the A chain of ricin covalently bonded to an antibody or an antibody fragment directed against an antigen in the cell to be destroyed.

2. A pharmaceutical composition according to claim 1, characterized in that the amine used is methylamine or one of its salts.

3. A pharmaceutical composition according to claim 1, characterized in that it is packaged for administration by the injectable route.

4. A pharmaceutical composition according to claim 1, characterized in that it is packaged for administration by the intravenous route.

* * * * *